United States Patent
Beghetto et al.

(10) Patent No.: US 11,104,767 B2
(45) Date of Patent: Aug. 31, 2021

(54) USE OF 2,4-DIHALO-6-SUBSTITUTED-1,3,5-TRIAZINES AND DERIVATIVE THEREOF AS CONDENSATION, CROSS-LINKING, TANNING, GRAFTING AND CURING AGENTS

(71) Applicant: CROSSING SRL, Treviso (IT)

(72) Inventors: Valentina Beghetto, Mestre (IT); Lodovico Agostinis, Mestre (IT)

(73) Assignee: CROSSING SRL, Treviso (IT)

( * ) Notice: Subject to any disclaimer, the term of this patent is extended or adjusted under 35 U.S.C. 154(b) by 0 days.

(21) Appl. No.: 16/311,486

(22) PCT Filed: Jun. 15, 2017

(86) PCT No.: PCT/EP2017/064720
§ 371 (c)(1),
(2) Date: Dec. 19, 2018

(87) PCT Pub. No.: WO2017/220435
PCT Pub. Date: Dec. 28, 2017

(65) Prior Publication Data
US 2019/0185627 A1  Jun. 20, 2019

(30) Foreign Application Priority Data

Jun. 22, 2016 (IT) .................. 102016000064894

(51) Int. Cl.
| | |
|---|---|
| C07D 251/26 | (2006.01) |
| C07D 251/44 | (2006.01) |
| C07D 251/50 | (2006.01) |
| C07D 251/52 | (2006.01) |
| C07D 251/64 | (2006.01) |
| C07D 413/04 | (2006.01) |
| C08K 5/3492 | (2006.01) |
| C08H 1/00 | (2006.01) |
| C14C 3/26 | (2006.01) |
| C08B 11/12 | (2006.01) |

(52) U.S. Cl.
CPC ............. *C08H 1/00* (2013.01); *C07D 251/26* (2013.01); *C08B 11/12* (2013.01); *C08K 5/3492* (2013.01); *C14C 3/26* (2013.01)

(58) Field of Classification Search
CPC .. C07D 251/26; C07D 251/44; C07D 251/50; C07D 251/52; C07D 251/64; C07D 413/04; C08K 5/3492; C08H 1/00
USPC ................. 530/409; 544/212, 209, 198
See application file for complete search history.

(56) References Cited

FOREIGN PATENT DOCUMENTS

| | | | |
|---|---|---|---|
| FR | 1369619 | 8/1964 | |
| JP | 2013139526 A * | 7/2013 | |
| WO | WO-2008124849 A2 * | 10/2008 | ........... C07D 519/00 |
| WO | 2015/044971 | 4/2015 | |
| WO | WO-2016103185 A2 * | 6/2016 | ............... C14C 3/26 |

OTHER PUBLICATIONS

Translation of the Japanese Patent Publication JP-2013139526-A. (Year: 2013).*
Shepherd et al., "The process of EDC-NHS Cross-linking of reconstituted collagen fibres increases collagen fibrillar order and alignment", APL Mater., vol. 3, No. 1: pp. 1-13 (Jan. 1, 2015).
El-Faham et al., "Peptide Coupling Reagents, More than a Letter Soup", Chem. Rev., vol. 111, pp. 6557-6602 (Aug. 26, 2011).
Written Opinion of the International Searching Authority and International Search Report dated Sep. 8, 2017 in International (PCT) Application No. PCT/EP2017/064720.
Kaminski et al., "Mild and Efficient Synthesis of Carboxylic Acid Anhydrides from Carboxylic Acids and Triazine Coupling Reagents", Synthetic Communications, vol. 34, No. 18, 2004, pp. 3349-3358.
Kunishima et al., "4-(4,6-Dimethoxy-1,3,5-triazin-2-yl)-4-methylmoipholinium Chloride: An Efficient Condensing Agent Leading to the Formation of Amides and Esters", Tetrahedron, vol. 55, 1999, pp. 13159-13170.

* cited by examiner

*Primary Examiner* — Joseph R Kosack
*Assistant Examiner* — Sagar Patel
(74) *Attorney, Agent, or Firm* — Wenderoth, Lind & Ponack, L.L.P.

(57) ABSTRACT

Use of 2,4-dihalo-6-substituted-1,3,5-triazines as condensing, cross-linking, tanning, grafting, curing agents for the production of amides, esters, thioesters, and stabilized collagen and leather, CMC (carboxymethyl cellulose), synthetic and natural polymers. The process enables to obtain non-toxic and totally free of heavy metals products characterized by Tg values between 80° C. and 100° C.

9 Claims, No Drawings

USE OF 2,4-DIHALO-6-SUBSTITUTED-1,3,5-TRIAZINES AND DERIVATIVE THEREOF AS CONDENSATION, CROSS-LINKING, TANNING, GRAFTING AND CURING AGENTS

FIELD OF APPLICATION OF THE INVENTION

The present invention relates to a process for the use of 2,4-dihalo-6-substituted-1,3,5-triazines and derivatives thereof, used in one step, as innovative condensation, cross-linking, tanning, grafting and curing agents, and for the preparation of compounds or high-value products such as drugs, synthetic or natural polymers, celluloses, collagen or highly stabilized leather.

PRIOR ART

The reactions for the formation of amides, esters and thioesters (condensation, cross-linking, tanning, grafting and curing) are of great importance in nature and organic chemistry.

In particular, condensation, crosslinking, tanning, grafting and curing reactions are all based on the same type of reaction, i.e. the formation of a covalent bond resulting in loss of one or more water molecules. However, since they involve specific reagent classes, we distinguish:

condensation reaction: reaction between a carboxylic acid and an amine, alcohol or thioalcohol, with the formation of an amide, ester or thioester;

cross-linking reaction: reaction between carboxylic groups and one or more amines, alcohols or thioalcohols in the same matrix or in uniformly dispersed matrices with the formation of one or more amides, esters or thioesters;

tanning reaction: is a particular type of cross-linking reaction, wherein the substrate is collagen, generally in the form of skin, powder or liquid;

grafting reaction: condensation reaction between a polymer or a polymeric surface having carboxylic, aminic, alcoholic or thioalcoholic functional groups and a chemical compound resulting in the formation of one or more molecules of water;

curing reaction: crosslinking reactions in different polymer chains resulting in the creation of amide covalent bonds, esters or thioesters.

The above mentioned condensation reactions are the basis of the synthesis processes of all biologically important macromolecules (polyamides, proteins, carbohydrates, lipids, nucleic acids), as well as for the production of a wide range of pharmaceuticals, polymers and fibers.

Condensation reactions are not spontaneous, so they need an activation step to form the desired product. Usually condensation occurs between an "activated" carboxylic acid, i.e. which has reached the transition state, whereby a minimum amount of additional energy is required to yield the products, such as, for example, acyl chlorides, mixed anhydrides or activated esters, and an amine, alcohol or thioalcohol. This can be obtained by heating to T>180° C., or under mild reaction conditions, for example at T 25-50° C. in the presence of an "activating" chemical reagent that lowers the activation energy level, that is, the energy to be administered to the system so that all reacting molecules reach the transition state. Carbodiimides are commonly employed in this type of reaction since in the presence of a carboxylic acid form an active intermediate species which, in the presence of an amine, alcohol or thioalcohol allows to obtain the corresponding amide, ester or thioester [A. El-Faham, Chem. Rev. 2011, 111, 6557-6602]. Dicyclohexyl-carbodiimide (DCC) is among the most commonly used carbodiimides; however, it requires the use of organic solvents and leads to the formation of a toxic co-product to be removed at the end of the reaction.

Alternatively, 1-ethyl-3-(3-dimethylaminopropyl) carbodiimide hydrochloride (EDC) can be used in water; however, to be efficient it requires the use of equimolar or higher amounts of N-hydroxysuccinimide (NHS). In addition, the EDC is poorly stable, should be stored at a low temperature (about −20° C.) and is very expensive. Despite the above disadvantages, EDC remains one of the most used reagents for the synthesis of polyaminoacids and other high-value pharmaceuticals, as well as for collagen cross-linking, tendon reconstruction, hydrogel production, protein synthesis, etc. [D. V. Shepherd, et al., APL Mater. 2015, 3, 1-13, U.S. Pat. No. 9,040,665 B2, US2012/0009223 A1].

An unexploited alternative concerns the use of 2-halo-4,6-dialkoxy-1,3,5-triazines derivatives and in particular of their quaternary ammonium salts, as an alternative to carbodiimides as described in the Italian patent application VE2014A00071, 102014902319159.

In the literature, there is only one example of usage of 2,4-dichloro-6-methoxy-1,3,5-triazine with the formation of 2-acyloxy-1,3,5-triazine, but it pertains to a totally unrelated field of application as it relates to the synthesis of anhydrides and not in condensation, cross-linking, tanning, grafting and curing for the preparation of compounds, polymers, collagen and highly stabilized leather [Kaminski et. Al Synth. Commun. 2004, 34, 3349-3358]. Kaminski et al. compare the activity of 2-chloro-4,6-dimethoxy-1,3,5-triazine (CDMT) with 2,4-dichloro-6-methoxy-1,3,5-triazine (MMT) and report (see data in table 1 pag. 3354-3355) four examples (4a, 4b, 4h, 4i) wherein the two reagents are employed in the presence of N-methylmorpholine for the synthesis of symmetric anhydrides. The results presented in Table 1 clearly show that, for the reported application, CDMT and MMT give comparable results, but MMT requires double amount of amine reagent to form the coupling agent, thus it is economically non-convenient.

Moreover, the data reported in Kaminski's paper are totally misleading and "teaching away" even the experts. In fact, according to Kaminsky's teaching, the alternative use of MMT instead of CDMT for the preparation of anhydrides seems to be discouraged, unlikely to the application of 2,4-dihalo-6-substituted-1,3,5-triazines for collagen stabilization, wherein, as demonstrated below, MMT results more efficient than CDMT.

Indeed, the 2,4-dichloro-6-methoxy-1,3,5-triazine subject matter of the present invention have been known for a very long time, as the French patent application FR 1 369 619 (1964) describes the synthesis process thereof, with a minor comment about their use as anticancer agents or pest controllers, but no hints about their possible use inherent to collagen treatment. Therefore, the herewith proposed used of 2,4-dichloro-6-methoxy-1,3,5-triazine relates to a completely different technical field than that described in this prior art document. Moreover, very remarkably, the procedure for the synthesis of 1,3,5-triazine derivatives reported in FR 1 369 619 is nowadays not applicable due to very high restrictions on solvents used in the described process, for example benzene which is carcinogenic and overall yields are rather modest (around 45%).

The international patent application WO2015/044971 and Kunishima et al. in Tetrahedron, Elsevier Science Publishers, Amsterdam, 1999, 55: 13159-13170, disclose the use of 4-(4,6-dimethoxy-1,3,5-triazin-2-yl)-4-methylmorpholinium chloride (DMTMM), respectively as tanning agent in the process of leather tanning and as condensing agent leading to the formation of amides and esters. Despite DMTMM and the compound of the present invention have the same, or equivalent, sostituents, i. e. DMTMM has two alkoxy groups and one quaternary ammonium group, whereas 2,4-disubstituted-6-substituted-1,3,5-triazines have one alkoxy group and two quaternary ammonium salts or halogen atoms, this does not imply that the activity and applicability of the two different classes of compounds should be comparable, and moreover the possibility to replace 2-chloro-4,6-disubstituted-1,3,5-triazines with 2,4-dihalo-6-substituted-1,3,5-triazines has in no way to be considered as obvious for the skilled person.

In fact, from a set of data of experiments carried out by the Applicant 2,4-dichloro-6-substituted-1,3,5-triazines resulted to be significantly more reactive than the corresponding 2-chloro-4,6-dialkoxy-1,3,5-triazines.

For example, the activity of 2,4-(6-methoxy-1,3,5-triazine-2,4-yl) bis-methylmorpholinum dichloride (MMTMM) and 4-(4,6-dimethoxy-1,3,5-triazin-2-yl)-4-methylmorpholinium chloride (DMTMM) have been compared in the condensation of benzoic acid and phenylethylamine in methanol for 15 minutes at room temperature (see scheme reaction below).

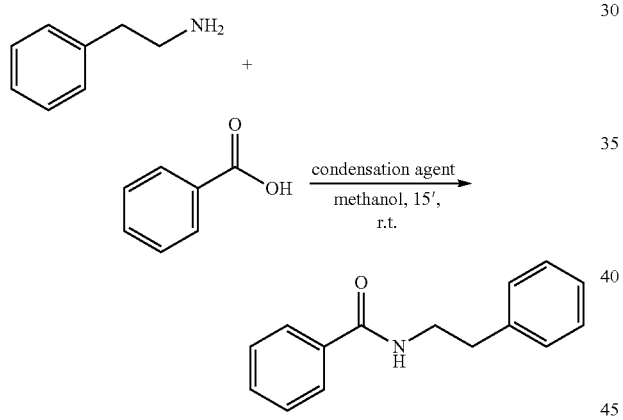

Reactions have been carried out as reported in Table 1.

TABLE 1

Formation of N-phenylethylbenzamide in the presence of different cross-linking agents (ACL)

| | ACL | Acid:amine:ACL | Yield (%) |
|---|---|---|---|
| Run 1 | DMTMM | 1:1:0.5 | 47 |
| Run 2 | MMTMM | 1:1:0.5 | 71 |

According to the literature, for each equivalent of acid to be activated an equivalent of DMTMM is required. Considering the yield values obtained in run 2 shown in Table 1, with a ratio substrate:condensation agent=1:0.5 and given that in several cases (only two cases are shown) the amide (N-phenylethylbenzamide) yield is greater than 50%, it is evident that the substitution of one alkoxy substituent on the triazine gives results which are not obvious and not derivable from prior art. In fact, for this application MMTMM is significantly more active than DMTMM.

Therefore to date, the need to have innovative condensation, cross-linking, tanning, grafting, curing agents, easy to be employed and without purification concerns at the end of the reaction is highly felt in the industrial and research field.

SUMMARY OF THE INVENTION

The object of the present invention is the use of 2,4-dihalo-6-substituted-1,3,5-triazines and derivatives thereof as innovative condensation, cross-linking, tanning, grafting, and curing agents for the preparation of high-value compounds such as drugs, synthetic or natural polymers, celluloses, collagen or highly stabilized leather.

DETAILED DESCRIPTION OF THE INVENTION

The object of the invention is the use of 2,4-dihalo-6-substituted-1,3,5-triazines, and derivatives thereof, as condensing agents, crosslinking, tanning, grafting, curing for the production of amides, esters, thioesters, collagen and stabilized leather, carboxymethylcellulose (CMC), synthetic and natural polymers.

Currently there are no studies or applications regarding the use of this class of compounds as condensation, cross-linking, tanning, grafting and curing agents.

These compounds are easy to be synthesized and used, are stable over time (also several months in solution) compared to alternative reagents known and used with the same purpose in the state of the art. The use of the compounds according to the invention also reduces the environmental impact of the process itself, limiting the amount of solvents and reagents, time required for their preparation and use.

Condensation grafting, tanning, crosslinking, curing agents used according to the invention are 2,4-dihalo-6-substituted-1,3,5-triazines of general formula I,

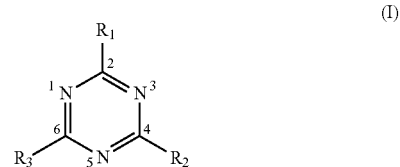

and derivatives thereof, wherein:

$R_1$ and $R_2$ are the same or different and are selected from the group consisting of: linear alkyl quaternary ammonium group, branched alkyl quaternary ammonium group, aryl quaternary ammonium group, heterocyclic quaternary ammonium group, Cl, Br and F.

$R_3$ is selected from the group consisting of: alkoxy (C1-C4), aryloxy (C6-C8) and substituted NR'R" wherein R' and R" independently are alkyl (C1-C4) or aryl (C6-C8);

In a preferred embodiment of the invention, $R_3$ is an alkoxy (C1-C4), and, in particular, is: $OCH_3$, $OCH_2CH_3$, $OCH(CH_3)_2$, $OCH_2CH_2CH_3$, $OCH_2CH_2CH_2CH_3$.

In another preferred embodiment of the invention, compound of general formula I, wherein $R_3$ is a substituted tertiary amine, whose amine substituents R' and R" independently are alkyl (C1-C4) or aryl (C6-C8), therefore in this embodiment $R_3$ is: $N(CH_3)_2$, $N(CH_2CH_3)_2$, $N[CH(CH_3)_2]_2$, $N(CH_2CH_2CH_2CH_3)_2$ and $N(C_6H_5)_2$ is used.

In a third preferred embodiment of the invention compound of general formula I, wherein $R_3$ is an aryloxy (C6-C8), and, in particular, is: $OC_6H_5$, $OCH_2C_6H_5$, $OCH_2C_6H_4CH_3$ is used.

In a fourth preferred embodiment, $R_1$ and $R_2$ are the same or different and are selected from the group consisting of linear or branched alkyl, aryl or heterocyclic quaternary ammonium salt.

In a further preferred embodiment $R_1$ and $R_2$ are independently selected from: Cl, Br and F.

According to the applicant's studies in the presence of Cl, Br and F in $R_1$ or $R_2$, condensation, cross-linking, tanning, grafting and curing reaction requires the presence of one or more equivalents of linear or branched, aryl or heterocyclic tertiary amine. Tertiary amines are used in combination with reagent I in the case $R_1$ and $R_2$ are selected from: Cl, Br and F, resulting in the formation of 2,4-diammonium derivatives of 2,4-dihalo-6-substitute-1,3,5-triazine which is the activating agent for the condensation reaction.

The use of tertiary amines is particularly preferred in this type of application as these do not interfere with condensation, cross-linking, tanning, grafting and curing reactions that can only be carried out from a primary or secondary amine according to the scheme:

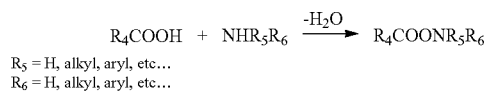

$R_5$ = H, alkyl, aryl, etc...
$R_6$ = H, alkyl, aryl, etc...

Hence, according to the invention in a particularly preferred embodiment the use of derivatives of 2,4-dihalo-6-substitute-1,3,5-triazine of general formula II

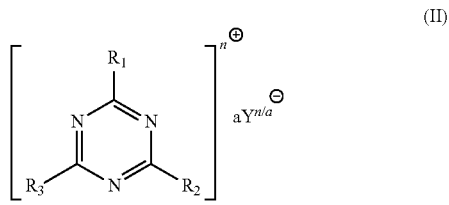

wherein $R_1$ and $R_2$ are the same or different and are selected from the group consisting of: linear or branched alkyl, aryl or heterocyclic quaternary ammonium group, Y is a counterion, having charge n/a from 1 to 4, a is between 2 and 4, and n is between 2 and 4; Y is a counterion selected from: Cl, Br and F, is provided.

$R_3$ is selected from the group consisting of: alkoxy (C1-C4), aryloxy (C6-C8) and substituted amine NR'R" wherein R' and R" independently are alkyl (C1-C4) or aryl (C6-C8);

According to the invention herein described, the process for the use of 2,4-dihalo-6-substituted-1,3,5-triazines and its derivatives comprises the following steps:

reaction between a reagent having carboxylic acid groups with one or more primary or secondary amines, alcohols or thioalcohols, in a single step, in a solvent, in the presence, depending on the type of specific reaction, e.g.: condensation, cross-linking tanning, grafting and curing, of the respective condensation, cross-linking, tanning, grafting and curing agent I as above described;

quenching the reaction by adding water and recovering the product according to standard techniques known to the field expert.

The solvent is selected from the group consisting of: aliphatic ether, halogenate, alcohol, ketone, ester, aromatic or aliphatic hydrocarbon, amide, carbonate, DMSO, water.

In particular, the above-specified procedure for the various types of reactions is:

Condensation reaction: reaction between 1 equivalent of carboxylic acid compound and 1-3 equivalents of primary or secondary amine, alcohol or thioalcohol, in an organic solvent or water in the presence of 1-3 equivalents of condensation agent I, as above described. The reaction is carried out at a temperature ranging from 0° C. to 70° C., for a time varying between 15 min and 6 hours. Reaction times are very short and purification procedures are very simplified with respect to the state of the art (Examples 9 and 10).

Cross-linking reaction: in this case the crosslinking reaction occurs between the carboxylic acid groups and primary or secondary amine groups, alcoholic or thioalcoholic groups present within the same matrix, in an organic solvent or water, in the presence of 1-20% by weight of crosslinking agent. In this case the reaction can occur in a homogeneous or heterogeneous phase depending on the nature of the treated matrix. For "homogeneous phase" in this description should be intended a reaction wherein in the same step all reagents are present; by the expression "heterogeneous phase" a reaction wherein the reagents are present in different phases is meant. The reaction is carried out at a temperature ranging from 0° C. to 70° C., for a time varying between 15 min and 6 hours (examples 3 and 4).

Tanning reaction: is a particular example of cross-linking reaction. Collagen, in form of powder, skin or liquid, is dispersed in water and 1-20% by weight of tanning agent is added. In this case the reaction can occur in a homogeneous or heterogeneous phase as the nature of the treated organic matrix varies. The reaction is carried out at a variable temperature ranging from 0° C. to 40° C., for a time varying from 15 minutes to 48 hours (examples 1-2).

The efficacy of the crosslinking degree obtained by the effect of 2,4-dihalo-6-substituted-1,3,5-triazines and their derivatives according to the invention is measured by DSC (Differential Scanning Calorimetry); a rise in Tg compared to non-crosslinked native collagen (Tg 60-65° C.) indicates an increase in the degree of crosslinking. In all cases, the collagen samples treated according to the invention have Tg values higher than 80° C., and in particular between 80° C. and 100° C.

To date there are no available tanning agents that can provide Tg values comparable to chromium salts (about 100° C.) that are used to produce more than 85% of tanned leather in the world, although chromium (III) is a heavy metal producing carcinogenic chromium (VI) and generating a high impact on the environment due to the formation of large quantities of sludge which should be disposed of.

The Tg values obtained according to the invention described herein by derivatives of I are a result of great value and innovation for the production of leather and for the collagen stabilization in general. In addition, as these reagents do not leave any traces in the final product, they enable to obtain highly stabilized, non-toxic, totally metal free leather and collagen.

Grafting reaction: reaction between a polymer having carboxylic acid groups, primary or secondary amines, alcohol or thioalcohol (in solution or solid) dispersed in a solvent or water and one or more carboxylic acids, primary or secondary amines, alcohols, thioalcohols in variable stoichiometry depending on the nature of the treated matrix. To this mixture, 0.1-3 equivalents of grafting agent I are added to the moles of acid, primary or secondary amines, alcohol, thioalcohol are added. In this case the reaction can occur in a homogeneous or heterogeneous phase as the nature of the treated matrix varies. The reaction is carried out at a temperature ranging from 0° C. to 70° C., for a time varying from 1 to 48 hours. Carboxylic acids, primary or secondary amines, alcohols and thioalcohols can be chosen to provide peculiar characteristics to the final polymers such as anti-fungal, anti-vegetative, anti-mould properties (examples 7 and 8). The grafting procedure of the present invention allows to modify the characteristics of polymers in a simple way, at high yield, and improved to the state of the art.

Curing reaction: reaction between a polymer having more carboxylic acid groups and one or more polymers having more primary or secondary amino groups, alcoholic, thioalcoholic in stoichiometry depending on the nature of the treated polymers. To this mixture is added 0.1-3 equivalents of curing agent I to the moles of acid, primary or secondary amine, alcohol, thioalcohol are added. In this case, the reaction can occur in a homogeneous or heterogeneous phase, depending on the nature of the polymeric matrix treated. The reaction is carried out at a temperature ranging from 0° C. to 70° C., for a time varying between 15 min and 48 hours (examples 5 and 6).

In the condensation, crosslinking, tanning, grafting and curing reactions in the presence of I, in the particular embodiment wherein $R_1=R_2=$Cl, Br or F, the condensation reagent I is used in combination with one or more tertiary amines that can be added to the reaction mixture simultaneously, or in succession, producing species of general formula II. Alternatively, reagents I and tertiary amines may be premixed in a solvent or water at a temperature between 0° C. and 50° C. for a time ranging from 15 minutes to 1 hour and then to be used for the reaction.

Based on the results obtained for the condensation, crosslinking, tanning, grafting and curing reactions it is evident that the combined use of the reagents I wherein $R_1=R_2=$Cl, Br or F and a tertiary amine according to the invention (see examples):

(i) provides conversions, performances and characteristics equal to or greater than those obtained by the use of reagent I having $R_2$ and $R_3$ other than a halogen;
(ii) may be formulated in the presence of different tertiary amines, and accordingly, depending on the type of application, one may choose the one available at the most advantageous market price;
(iii) has no problem of activity related to the nature of the solvent.

The effectiveness of the process according to the invention has been tested in various condensation reactions between a carboxylic acid and an amine, alcohol or thioalcohol, as widely described in the examples of the experimental section.

Experimental Part

The invention will now be below described with particular reference to some non limitative examples.

Example 1. Collagen Tanning in the Presence of the Derivative I Having $R_3=$OCH$_3$, $R_1=R_2=$N-ethylmorpholine In a becker equipped with magnetic stirrer, 250 mg of collagen in powder were suspended in 20 ml of water and 31 mg (0.075 mmoles) of I. After 4 hours at room temperature the suspension was filtered and collagen analyzed by DSC (Tg=84° C.)

Example 2. Collagen Tanning in the Presence of I Having $R_3=$OCH$_3$, $R_1=R_2=$Cl and N-methylmorpholine In a becker equipped with magnetic stirring, 250 mg of powdered collagen were suspended in 20 mL of water, 12-50 mg (0.075-0.35 mmol) of I and 7.6-35.4 mg (0.075-0.35 mmol) of N-methylmorpholine. After 4 hours at room temperature, the suspension was filtered and collagen analyzed by DSC, providing Tg=82-90° C. at varying the moles of reagents employed.

Example 3. CMC Cross-Linking in the Presence of I Having $R_3=$OCH$_3$, $R_1=R_2=$N-methylmorpholine In a magnetically stirred balloon 280 mg of CMC (carboxylation degree c=0.7) were dissolved in 25 ml of water and 20 mg (0.05 mmoles) of I. After 24 hours at r.t., the CMC was filtered, washed and characterized by FT-IR: 3200, 1750-1735, 1602, 1020 cm$^{-1}$.

Example 4. CMC Cross-Linking in the Presence of I Having $R_3=$OCH$_3$, $R_2=R_3=$Cl and N-ethylmorpholine In a magnetically stirred balloon 280 mg of CMC (c=0.7), 25 ml of water, 12-50 mg (0.075-0.35 mmoles) of I and 8.6-40.3 mg (0.075-0.35 mmoles) of N-ethylmorpholine were added. After 24 hours, the CMC was filtered, washed and characterized by FT-IR.

Example 5. Curing of CMC/Chitosan in the Presence of I Having $R_3=$N(CH$_2$CH$_3$)$_2$, $R_1=R_2=$N-methylpyrrolidinium In a magnetically stirred balloon, 50 mL of water, 1 g of CMC (c=0.7), 250 mg of chitosan and 50 mg (0.13 mmoles) of I were introduced. After 24 hours, the product was filtered, washed and characterized by FT-IR: 3200.3000, 1750-1735, 1602, 1020, 890 cm$^{-1}$.

Example 6. Curing of CMC/Chitosan in the Presence of I Having $R_3=$N(CH$_2$CH$_3$)$_2$, $R_1=R_2=$Cl and N-methylpyrrolidine In a magnetically stirred balloon, 50 mL of water, 1 g of CMC=0.7), 250 mg of chitosan, 13.5-63 mg (0.075-0.35 mmoles) of I and 6.3-30.0 mg (0.075-0.35 mmoles) of N-methylpyrrolidine were added. After 24 hours, the product was filtered, washed and characterized by FT-IR.

Example 7. Polyacrylic Acid Grafting with Taurine in the Presence of I Having $R_3=$OCH$_3$, $R_1=R_2=$N-trimethylammonium In a balloon equipped with magnetic stirrer, 600 mg of polyacrylic acid, 500 mg of taurine (3.8 mmoles), 15 mL water and 630 mg (2.1 mmoles) of I. After 24 hours, the obtained white solid was filtered, washed, dried and characterized by NMR. 1H NMR (300 MHz, DMSO D6, ppm) δ: 4.36 (1H, s), 4.23 (2H, s)

Example 8. Polyacrylic Acid Grafting with Taurine in the Presence of I Having $R_3$=OCH$_3$, $R_1$=$R_2$=Cl and N-trimethylamine In a balloon equipped with magnetic stirrer, 600 mg of polyacrylic acid, 500 mg of taurine (3.8 mmoles), 15 mL of water, 270-450 mg (1.5-2.5 mmoles) of I and 89.0-147.5 mg (1.5-2.5 mmoles) of N-trimethylamine. After 24 hours, the obtained solid is filtered, washed, dried and characterized by NMR.

Example 9. Condensation of Benzoic Acid in the Presence of I Having $R_3$=OCH$_3$, $R_1$=$R_2$=N-trimethylammonium In a balloon equipped with magnetic stirring, 146 mg (1.2 mmol) of phenylethylamine, 147 mg (1.2 mmol) of benzoic acid, 6 mL of methanol and 230 mg (0.6 mmol) of I were added. After 3 hours at a temperature between 0° C. and 50° C., the solvent was removed and the solid residue was dissolved in diethyl ether (30 mL), was washed with an aqueous solution of Na$_2$CO$_3$, then with a 1N solution of HCl, made anhydrous with MgSO$_4$ and filtered. The solution was dehydrated to obtain a white solid (yield 92%, purity 95%). H NMR (300 MHz, CDCl$_3$, ppm) δ: 7.8-7.2 (10H, m), 6.20 (1H, s broad), 3.71 (2H, q), 2.95 (2H, t).

Example 10. Condensation of Benzoic Acid and Phenylethylamine in the Presence of I Having $R_3$=OCH$_3$, $R_1$=$R_2$=Cl and N-methylmorpholine In a balloon equipped with magnetic stirring, 146 mg (1.2 mmol) of phenylethylamine, 147 mg (1.2 mmol) of benzoic acid, 4 mL of methanol, 108-180 mg (0.6-1.0 mmol) of I and 60.6-101.5 mg (0.6-1.0 mmol) of N-methyl morpholine were added. After 1 hour, the reaction mixture was treated as described in Example 9 (yield 95% purity 93%).

The invention claimed is:

1. A method for condensing, cross-linking, tanning, grafting, or curing, comprising:
   (a) reacting a reagent having a carboxylic acid group with at least one primary or secondary amine, alcohol or thioalcohol in a solvent and in the presence of a 2,4,6-substituted-1,3,5-triazine of formula (I),

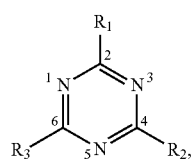

wherein $R_1$ and $R_2$ are independently selected from the group consisting of linear alkyl quaternary ammonium group, branched alkyl quaternary ammonium group, aryl quaternary ammonium group, and heterocyclic quaternary ammonium group, and $R_3$ is selected from the group consisting of (C1-C4)alkoxy, (C6-C8)aryloxy, and a substituted amine of the formula NR'R", wherein R' and R" are independently (C1-C4)alkyl or (C6-C8) aryl, and (b) quenching the reaction by adding water to recover a condensed, cross-linked, tanned, grafted or cured reaction product.

2. The method according to claim 1, wherein $R_3$ is selected from the group consisting of OCH$_3$, OCH$_2$CH$_3$, OCH(CH$_3$)$_2$, OCH$_2$CH$_2$CH$_3$, and OCH$_2$CH$_2$CH$_2$CH$_3$.

3. The method according to claim 1, wherein $R_3$ is selected from the group consisting of OC$_6$H$_5$, OCH$_2$C$_6$H$_5$, OCH$_2$C$_6$H$_4$CH$_3$.

4. The method according to claim 1, wherein $R_3$ is selected from the group consisting of N(CH$_3$)$_2$, N(CH$_2$CH$_3$)$_2$, N[CH(CH$_3$)$_2$]$_2$, N(CH$_2$CH$_2$CH$_2$CH$_3$)$_2$ and N(C$_6$H$_5$)$_2$.

5. The method according to claim 1, wherein the reacting step (a) is carried out at a temperature between 0° C. and 70° C. for 15 minutes to 48 hours.

6. The method according to claim 1, wherein the solvent is selected from the group consisting of an aliphatic ether, a halogenate, an alcohol, a ketone, an ester, an aromatic hydrocarbon, an aliphatic hydrocarbon, an amide, a carbonate, DMSO and water.

7. The method according to claim 1, comprising reacting collagen dispersed in water in the presence of 1-20% by weight of the 2,4,6-substituted-1,3,5-triazine of formula (I) at a temperature of 0° C. to 40° C. for 15 minutes to 48 hours, and wherein the collagen is in the form of powder, skin or liquid.

8. A method for condensation, cross-linking, tanning, grafting or curing for the production of amides, esters, thioesters, stabilized collagen, leather, and natural and synthetic polymers, comprising the steps of:
   (a) reacting a reagent having a carboxylic acid group with at least one primary or secondary amine, alcohol or thioalcohol in a solvent and in the presence of a 2,4,6-substituted-1,3,5-triazine of formula (I),

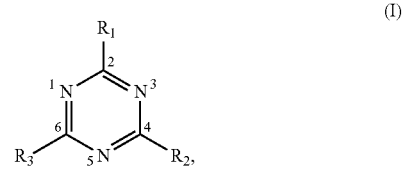

wherein $R_1$ and $R_2$ are independently selected from the group consisting of linear alkyl quaternary ammonium group, branched alkyl quaternary ammonium group, aryl quaternary ammonium group, and heterocyclic quaternary ammonium group, $R_3$ is selected from the group consisting of (C1-C4)alkoxy, (C6-C8)aryloxy, and a substituted amine of the formula NR'R", wherein R' and R" are independently (C1-C4)alkyl or (C6-C8) aryl, and (b) quenching the reaction by adding water.

9. The method according to claim 8, comprising reacting collagen dispersed in water in the presence of 1-20% by weight of the 2,4,6-substituted-1,3,5-triazine of formula (I) at a temperature of 0° C. to 40° C. for 15 minutes to 48 hours, and wherein the collagen is in the form of powder, skin or liquid.

* * * * *